United States Patent [19]

Kaiser

[11] 4,134,904
[45] Jan. 16, 1979

[54] SYNTHESIS OF STEROIDS

[76] Inventor: Emil T. Kaiser, 5634 S. Woodlawn Ave., Chicago, Ill. 60637

[21] Appl. No.: 829,009

[22] Filed: Aug. 30, 1977

[51] Int. Cl.$^2$ .............................. C07J 9/00; C07J 1/00
[52] U.S. Cl. ............................ 260/397.1; 260/397.2; 260/397.5
[58] Field of Search ................ 260/397.2, 397.1, 397.5

[56] References Cited

U.S. PATENT DOCUMENTS

| | | | |
|---|---|---|---|
| 3,152,152 | 10/1964 | Wechter | 260/397.2 |
| 3,257,384 | 6/1966 | Nelson | 260/397.2 |

Primary Examiner—Elbert L. Roberts
Assistant Examiner—Robert C. Whittenbough
Attorney, Agent, or Firm—Carl C. Batz

[57] ABSTRACT

The synthesis of 25-hydroxycholesterol from animal bile starting materials in which hyodeoxychloic acid or an ester thereof is converted to the 3β-hydroxy-5-cholenic acid alkyl ester, and then converted to 3β-hydroxy-25-cyano-5-cholene by a series of steps in which the sterol nucleus is stablized by use of a 3α,5α-bridge sometimes called an i-steroid configuration, and the carbon chain then extended from the carbon at the 24-position to a cyanide group at the 25-position. The compound so formed is subjected to a series of reactions by which it is transformed into 25-hydroxy-7-dehydrocholesterol which may then be irradiated with ultraviolet light to 25-hydroxycholecalciferol. The invention discloses new and improved processes for preparing these end products and also the compounds formed as intermediates and processes for preparing these intermediates.

7 Claims, No Drawings

SYNTHESIS OF STEROIDS

This invention relates to cholecalciferol derivatives having biological activity and to processes and compounds useful in the synthesis of such compounds and derivatives. More particularly this invention relates to the synthesis of 25-hydroxycholesterol and 25-hydroxycholecalciferol and to compounds and processes useful in the synthesis of these compounds.

BACKGROUND OF THE INVENTION

Vitamin $D_3$, which is cholecalciferol, has been known for many years. It may be prepared from cholesterol by the introduction of an additional bond into the cholesterol molecule to produce 7-dehydrocholesterol and subjecting the 7-dehydrocholesterol to ultraviolet irradiation. It was at one time thought to be biologically active in the regulation of intestinal calcium transport and the mobilization of calcium from bone.

Recently, it has been discovered that to be biologically active the cholecalciferol has to be hydroxylated in the body to 25-hydroxycholecalciferol or certain derivatives thereof, and it is the 25-hydroxycholecalciferol and derivatives thereof which are active in regulating intestinal calcium transport and mobilization of calcium from bone. It would, therefore, be important to prepare and administer 25-hydroxycholecalciferol instead of Vitamin $D_3$.

It is known that 25-hydroxycholecalciferol can be produced by ultraviolet radiation of its provitamin 25-hydroxy-7-dehydro-cholesterol but it has not heretofore been possible to obtain 25-hydroxycholesterol except in amounts so small as to make it impractical for use in the preparation of 25-hydroxycholecalciferol. The transformation of 25-hydroxycholesterol to 25-hydroxy-7-dehydrocholesterol and the preparation of 25-hydroxycholecalciferol from the 7-dehydro compound by irradiation with ultraviolet light was described by J. W. Blunt and H. F. DeLuca in *Biochemistry* 8, 671 (1969). The biological activity of the synthetic 25-hydroxycholecalciferol was also assayed by the same authors, and the results published in their paper.

Sources from which 25-hydroxycholesterol has been prepared in small amounts include: cholesterol, stigmasterol 3β-hydroxypregn-5-ene (synthesized from a natural source) and ergosterol (from which 25-hydroxy-7-dehydrocholesterol may be obtained). Yields in these syntheses are usually poor, chemicals needed for carrying out the procedures may have to be specially prepared, and in some cases special equipment is required which may not be conveniently available in a plant producing industrial chemicals.

The synthesis of 25-hydroxycholesterol by E. J. Semmler, M. F. Holic, H. K. Schnoes and H. F. DeLuca (*Tetrahedron Letters*, 4147 (1972)) begins with the oxidation of cholesterol. The oxidation product is converted to i-homocholanic acid methyl ether which is esterified with diazomethane, a dangerous, explosive compound. Then by a number of steps a hydroxyl group is introduced into position 6. Without counting the preparation of i-homocholanic acid, 18 steps are required to introduce the hydroxyl groups. Further, the scarcity of the starting materials makes the method impractical for large scale manufacture.

Accordingly, I have set about to discover new syntheses of 25-hydroxycholecalciferol, and particularly a new synthesis of 25-hydroxy-7-dehydrocholesterol. I have sought such a synthesis for which a starting material is readily available and in which high yields of 25-hydroxycholesterol of 25-hydroxycholecalciferol may be obtained. Further, I have sought syntheses in which the chemicals necessary for conducting the necessary reactions are commercially available and reasonably priced and I have sought such syntheses which utilize equipment generally available in chemical manufacturing plants so as to avoid the need for large capital investments.

In my co-pending patent application Ser. No. 816,478 filed July 18, 1977 I disclosed new and effective syntheses of 25-hydroxycholesterol in which hyodeoxycholic acid or an ester thereof obtained from hog bile is converted to 3β-hydroxy-5-cholanic acid, this compound protected in the 3-position of the sterol nucleus with an aliphatic or heterocyclic group in an ether linkage, and this converted by a series of steps to a 25-cyano derivative and this, in turn, converted by a series of steps to 25-hydroxycholesterol.

SUMMARY

I have now discovered new and different syntheses in which the 3-position of 3β-hydroxy-5-cholenic acid alkyl ester is converted to 6β-alkoxy-3α,5α-cyclocholanic acid alkyl ester, also called a 6β-alkoxy-i-steroid derivative. In this i-steroid derivative, the 3-position is protected by a cyclic structure which is stable to alkaline reducing agents. The compound so formed may be subjected to a series of reactions by which it is transformed into 25-hydroxycholesterol which, in turn, may be converted to 25-hydroxy-7-dehydrocholesterol which may be irradiated with ultraviolet light to yield 25-hydroxycholecalciferol.

DISCLOSURE OF THE INVENTION

The synthesis starts with hyodeoxychloric acid or an ester thereof, preferably the methyl ester, which is converted to the 3β-hydroxy-5-cholenic acid ester. Synthesis of 3β-hydroxy-5-cholenic acid is known and is set forth in detail in an article by K. R. Barucha, G. C. Buckley, C. K. Cross, L. R. Rubin and P. Ziegler in *Can. J. Chem.*, 34, 982 (1956) and in Example 1 of my pending application Ser. No. 816,478.

The next series of steps in the synthesis involves the placement of a protective group at the 3-position to stabilize the steroid nucleus during subsequent reactions involving alkaline reducing agents preliminary to the sidechain extension by one carbon. This protection, according to the present invention, includes an i-steroid structure which is obtained by a two-step procedure which I will now explain.

3β-hydroxy-5-cholenic acid ester which has the following structure and is designated as Compound 1:

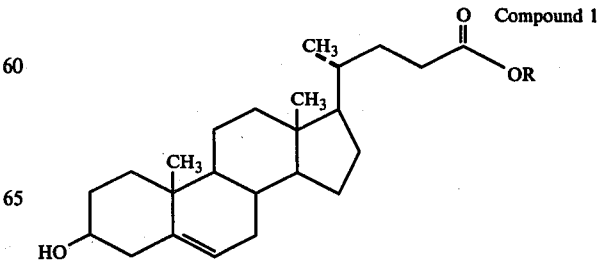

where R is an alkyl, aryl or cyclic group is mixed in pyridine with p-toluenesulfonyl chloride to obtain the 3-tosyl ester, designated Compound 2, and having the following structure:

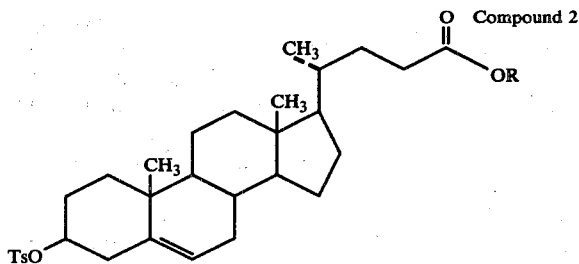

where R is an alkyl, aryl or cyclic group.

In this application the term "alkyl" is understood to include the unsaturated form as well as the saturated form.

Compound 2 may be mixed with pyridine in an alcoholic solution, preferably methanol, and refluxed. Usually refluxing for a few hours is sufficient to complete the reaction to obtain the 6β-alkoxy-3α,5α-cyclocholanic acid ester designated Compound 3 and having the following structure:

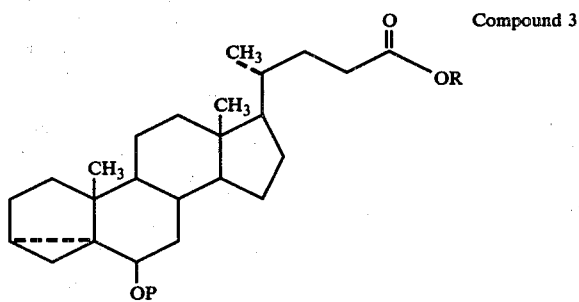

where R is an alkyl, aryl or cyclic group, and P is an aliphatic group, preferably methyl.

The yield of Compound 3 may be as high as 70% or greater. The side reaction product may be obtained which is identified as the 3-methoxy-5-cholenic acid alkyl ester designated as Compound 3a and having the following structure:

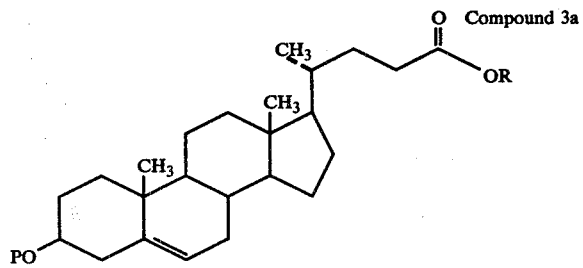

where R is an alkyl, aryl or cyclic group, and P is an aliphatic group, preferably methyl.

Following the two-step procedure above described, Compound 3 may be treated with a reducing agent to reduce the 24-carboxylic acid ester group to a 24-hydroxyl group. The reducing agent may be a complex of aluminum hydride with sodium, potassium or lithium. This complex does not affect the i-steroid configuration of Compound 3. The reduction in one of its forms may be carried out in benzene solution with sodium bis(2-methoxyethoxy) aluminum hydride (Vitride) or with lithium aluminum hydride by refluxing for a period sufficient to complete the reaction, for example, about 1½ hours. The compound so obtained with the preferred protecting group, 3α,5α-cyclo-6β-methoxy-24-hydroxycholane, has the following structure and is designated Compound 4:

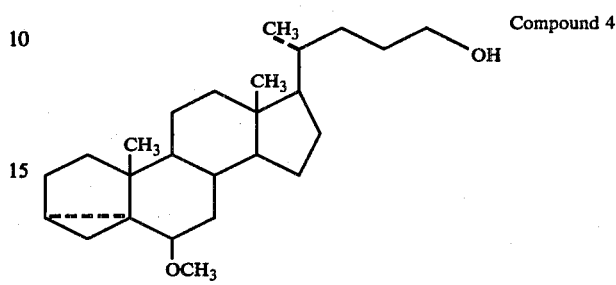

Compound 4 may be mixed with p-toluenesulfonyl halide in pyridine solution and allowed to react to replace the hydroxyl group with OTs to obtain Compound 5 which may be written:

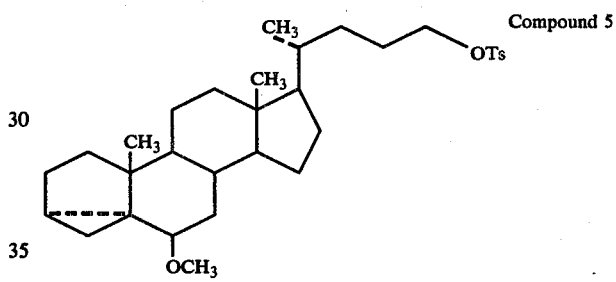

Compound 5 may be mixed with and allowed to react with a metallic cyanide, preferably potassium cyanide, but other metallic cyanides such as sodium cyanide, lithium cyanide or silver cyanide may also be used to replace the sulfonyl ester function of Compound 5 with CN. The crucially important extension of the side chain by one carbon atom has now been accomplished without affecting the i-steroid nucleus.

In one of its forms, the reaction of Compound 5 and potassium cyanide may be carried out by heating in dimethylformamide (DMF) for a period until the reaction is complete, for example, at about 97° C. for about 18 hours. The resulting compound is 6β-methoxy-25-cyano-3α,5αcyclocholane which is designated Compound 6 and has the structure:

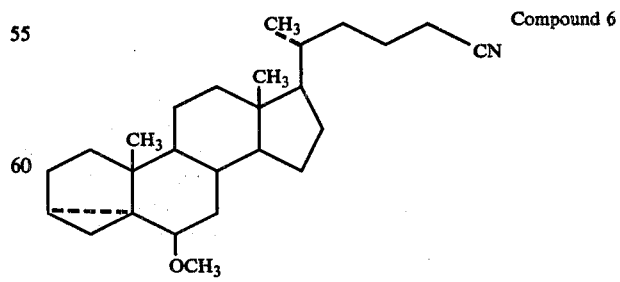

The 3-hydroxy group of Compound 6 may be restored by dissolving it in a water-dioxane mixture, adding p-toluenesulfonic acid and heating, for example, to about 80° C. for about 4½ hours. The resulting compound is 3β-hydroxy-25-cyano-5-cholene which is designated Compound 7 and has the following structure:

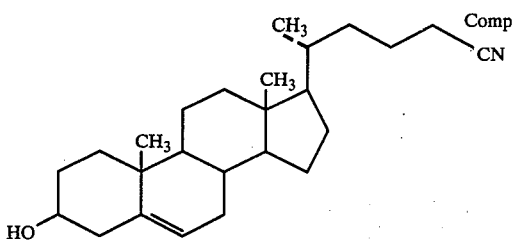

Compound 7 has the same structure and is identical to Compound J of my prior application Ser. No. 816,478 filed July 18, 1977 and the disclosure concerning the conversion of 3β-hydroxy-25-cyano-5-cholene to 25-hydroxycholesterol and the conversion of 25-hydroxycholesterol to 25-hydroxycholecalciferol contained in said application Ser. No. 816,478, including examples 9 to 12 of that application, is incorporated by reference in this application.

Specific examples illustrating how the reactions herein described may be carried out are given as follows:

EXAMPLE 1

Preparation of 3β-hydroxy-5-cholenic acid methyl ester p-toluenesulfonate 13.1 g of 3β-hydroxy-5-cholenic acid methyl ester, 0.034 mole, and 8 g of p-toluenesulfonyl chloride, 0.042 mole, were dissolved in 15 ml pyridine at room temperature. After standing for 48 hours at about 3° C., the mixture was poured into 135 ml of ice cold water. With stirring, 6 ml of conc HCl was added, and stirring and cooling were continued for ½ hour. The precipitate was removed by filtration, washed with water and dried. 17.8 g of slightly colored material was obtained, yield 97%, mp 119°–121° C. (989-99-A). Anal. Calcd for $C_{32}H_{46}SO_5$, M.W. 542.785: C, 70.81; H, 8.54; S, 5.91. Found: C, 70.64; H, 8.66; S, 5.73. NMR, 989-64A (CDCl$_3$): δ7.18–7.90 (AB$_q$, 4H, aromatic), 5.20–5.36 (m, 1H, vinyl) 4.12–4.50 (br m, 1H,

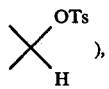

), 3.65 (s, 3H, —OCH$_3$), 2.44 (s, 3H, —ArCH$_3$), 0.97 (s, 3H, C-19 —CH$_3$), 0.66 (s, 3H, C-18 —CH$_3$). IR (989-99-A) (CHCl$_3$): 2955, 1735, 1445, 1365, 1195, 1180, 940, 900, 875 cm$^{-1}$. Mass spectrum (989-48-A). m/e 370 (M-172), 355, 339, 262, 255, 249, 213.

EXAMPLE 2

Preparation of 6β-methoxy-3α,5α-cyclocholanic acid methyl ester 6.1 g (0.0112 mole) of 3β-hydroxy-5-cholenic acid methyl ester p-toluenesulfonate, 1.78 g (0.0224 mole) of pyridine and 750 ml methanol were stirred and refluxed for 3 hours. After cooling, the reaction mixture was evaporated under reduced pressure. The residue was dissolved in chloroform, washed with water, dried and evaporated. The residue weighed 4.51 g, corresponding to the weight calculated for the crude product. This material was re-dissolved in ether, washed with 10% sulfuric acid, then with a saturated sodium bicarbonate solution, dried, and evaporated. NMR data indicated that this viscous liquid residue contained two products. The main component, about 75%, was the desired compound, the 6β-methoxy-3α,5α-cyclocholanic acid methyl ester, and the byproduct, about 25%, was the 3-methoxy-5-cholenic acid methyl ester.

The two components were separated by crystallizing from methanol the 3β-methoxy-5-cholenic acid methyl ester (mp 106°–108° C.) while the 3α,5α-cyclo derivative remained dissolved in the mother liquor. After evaporation of the solvent, the residue was a colorless viscous oil, identified by IR and NMR to be 6β-methoxy-3α,5α-cyclocholanic acid methyl ester (789-54-A-III).

EXAMPLE 3

Separation of 6β-methoxy-3α,5α-cyclocholanic acid methyl ester from 3β-methoxy-5-cholenic acid methyl ester As described in Example 2, 3β-hydroxy-5-cholenic acid methyl ester p-toluenesulfonate, pyridine and methanol were refluxed for 3 hours, the solution evaporated, the residue dissolved in ether, washed with 10% sulfuric acid and with a saturated sodium bicarbonate solution. The ether was evaporated after drying.

12.3 g of this ether residue was dissolved in 120 ml methanol. The solution was seeded with a few crystals of 3β-methoxy-5-cholenic acid methyl ester, obtained from separation experiments in Example 2. Crystals separated overnight and were removed by filtration. They weighed 2.43 g after drying. This was the 3β-methoxy-5-cholenic acid methyl ester.

The mother liquor was evaporated and 9.38 g of a pale, viscous oil was obtained. The yield of 6β-methoxy-3α,5α-cyclocholanic acid methyl ester, was 72% (985-105). NMR (989-105-B) (CDCl$_3$): δ3.63 (s, 3H,

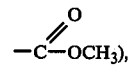

3.25 (s, 3H, —OCH$_3$), 2.75 (m, 1H,

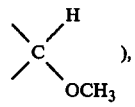

1.02 (s, 3H, C-19 —CH$_3$), 0.71 (s, 3H, C-18 —CH$_3$). IR (989-105-B) (CHCl$_3$): 2940, 2860, 1725, 1440, 1175, 1100 cm$^{-1}$.

EXAMPLE 4

Preparation of 6β-methoxy-24-hydroxy-3α,5α-cyclocholane 13.2 ml of sodium bis(2-methoxyethoxy) aluminum hydride (Vitride), 70% solution, and 100 ml of benzene were stirred and heated to reflux in an atmosphere of nitrogen. A solution in 40 ml benzene of 8 g of 6β-methoxy-3α,5α-cyclocholanic acid methyl ester, obtained as the methanol residue of Example 3, was added dropwise in 1 hour and refluxing under nitrogen was continued for 1½ hours. Heating was then discontinued, and the reaction mixture stirred for 3 more hours. 100 ml of 20% aq. hydrochloric acid was added, the mixture was stirred one hour and the aqueous layer separated. The benzene layer was washed with water, dried, decolorized with charcoal and evaporated. An oil was obtained, weighing 7.5 g. Analytical determinations indicated a quantitative reduction of the ester group to the 24-hydroxyl group, yield 100% (989-109). NMR (989-109-A) (CDCl$_3$): δ3.40-3.60 (br t, 2H —C$\underline{H}_2$OH), 3.30 (s, 3H, —OCH$_3$), 2.75 (m, 1H,

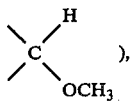

2.21 (s, 1H, —OH), 1.00 (s, 3H, C-19 —CH$_3$), 0.61 (s, 3H, C-18 —CH$_3$). IR (989-109-A) (CHCl$_3$): 3640, 3450, 1475, 1390, 1190, 1105, 1080, 1025 cm$^{-1}$.

EXAMPLE 5

Preparation of 6β-methoxy-24-(p-toluenesulfonoxy)-3α,5α-cyclocholane 8 g of a product, containing a mixture of 6β-methoxy-24-hydroxy-3α,5α-cyclocholane and 3β-methoxy-24-hydroxy-5-cholene, and 5.4 g of p-toluenesulfonyl chloride were dissolved in 45 ml pyridine and the mixture kept at about 3° C. for 46 hours. Then it was poured into 120 ml of a water-ice mixture, and the pH adjusted to 3 with hydrochloric acid. The milky mixture was diluted with 500 ml water and extracted with a mixture of 300 ml chloroform and 100 ml ether. The organic layer separated overnight, and from it a viscous oil was obtained. This oil was extracted with ether and the ether extract removed by decantation from an insoluble substance.

The ether solution was washed with water, dried, decolorized with charcoal and evaporated to dryness. The residue, a viscous liquid, was the expected tosylate. It weighed 8.8 g, yield 73% (989-120A). NMR (989-120A) (CDCl$_3$): δ7.20-7.90 (AB 4H, Ar-H), 3.85-4.15 (br t, 2H, —C$\underline{H}_2$OTs), 3.30 (s, 3H, —O—CH$_3$), 2.70-2.82 (m, 1H,

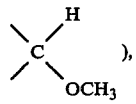

2.45 (s, 3H, Ar —CH$_3$), 1.01 (s, 3H, C-19 —CH$_3$), 0.60 (s, 3H, C-18 —CH$_3$). IR (989-120-A) (CHCl$_3$): 2925, 2860, 1600, 1460, 1360, 1190, 1180, 1100, 965, 920 cm$^{-1}$.

EXAMPLE 6

Preparation of 6β-methoxy-25-cyano-3α,5α-cyclocholane 8.62 g (0.16 mole) 6β-methoxy-24-(p-toluenesulfonoxy)-3α,5α-cyclocholane, prepared according to Example 5, and 6.4 g powdered potassium cyanide (0.098 mole) were added to 535 ml DMF, and the stirred mixture heated in an oil bath at 97° C. for 18 hours. After cooling, the reaction mixture was poured into 2.1 liters of water and extracted with ether. The ether layer was washed with water and evaporated. The residue from the concentrated aqueous washed with dissolved in chloroform, washed with water, dried and evaporated. The resulting viscous oil obtained upon combination of above samples was the expected cyano compound, according to analytical data. It weighed 6.22 g, yield 99% (989-125 A + B). NMR (989-97-A) (CDCl$_3$): δ3.30 (s, 3H, —OCH$_3$), 2.70-2.85 (m, 1H,

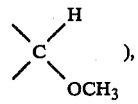

2.10-2.40 (m, 2H, —CH$_2$—CN), 1.02 (s, 3H, C-19 —CH$_3$), 0.72 (s, 3H, C-18 —CH$_3$). IR (989-97-A) (CHCl$_3$): 2910, 2875, 2255, 1460, 1380, 1100, 1080, 1020 cm$^{-1}$.

EXAMPLE 7

Preparation of 3β-hydroxy-25-cyano-5-cholene 7.6 g of 6β-methoxy-25-cyano-3α,5α-cyclocholane was dissolved in 100 ml dioxane. Added to this solution were 100 ml water and 0.49 g of p-toluenesulfonic acid (6.5% of the cyano compound). The mixture was kept for 4½ hours in an oil bath at 80° C. and then left at room temperature overnight. The precipitated product was removed by filtration, washed with water and the white solid dried. By fractional crystallizations from n-heptane several crops of crystals were obtained. The combined weight of these fractions was 4.5 g. Melting points varied; the highest one was 175°-182° C. All were the desired 3β-hydroxy-25-cyano-5-cholene, according to the analytical data. The yield of the combined fractions was 61%. By recrystallization a sample of mp 183°-186° C. was obtained and C, H and N determinations were carried out. Anal. Calcd for C$_{25}$H$_{39}$NO, M.W. 369.596: C, 81.24; H, 10.64; N, 3.79; O, 4.33. Found: C, 81.04; H, 10.67; N, 3.78; O, 4.16 (989-182-A-I). NMR (939-182-A-I) (CDCl$_3$): 5.20-5.40 (m, 1H, vinyl), 3.25-3.65 (m, 1H,

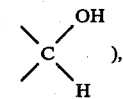

1.75 (s, 1H, —OH) 1.00 (s, 3H, C-19 —CH$_3$), 0.68 (s, 3H, C-18 —CH$_3$). IR (989-182-A-I) (CHCl$_3$): 3610, 3450, 2940, 2870, 2255, 1470, 1385, 1050, 1025 cm$^{-1}$. Mass spectrum: m/e 369 (M$^+$), 351, 336, 258.

While only certain embodiments of my invention are disclosed in detail it will be apparent to those skilled in the art that many embodiments may be practiced and many changes may be made all within the spirit of the invention and the scope of the appended claims.

What is claimed is:

1. A steroid compound having the structure

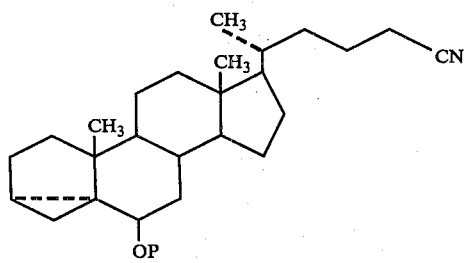

where P is an alkyl group.

2. A steroid compound as set forth in claim 1 where P is methyl.

3. In a process for preparing 25-hydroxycholesterol the step of heating with a metal cyanide a compound having the structure:

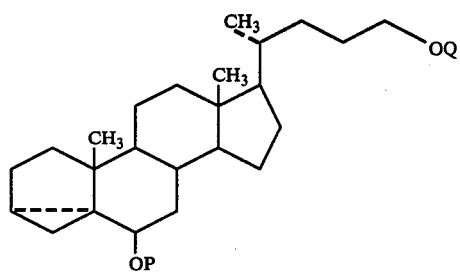

where P is an alkyl group and Q is an alkyl sulfonyl or aryl sulfonyl group, in dimethylformamide to obtain the compound having the structure:

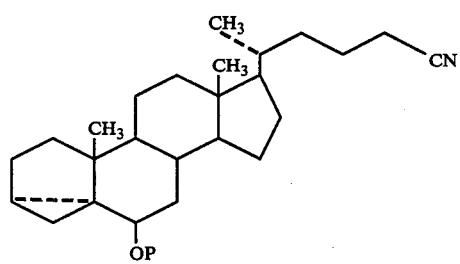

where P is an alkyl group.

4. A process as set forth in claim 3 wherein P is a methyl group and Q is a p-toluenesulfonyl group.

5. In a process for preparing 25-hydroxycholesterol the step of heating a compound having the structure

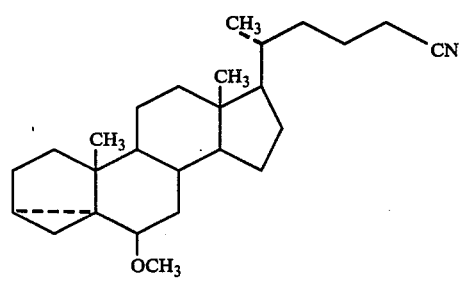

in aqueous alcohol, dioxane or tetrahydrofuran, containing p-toluenesulfonic acid, for a period until the reaction is complete, to obtain a compound having the structure

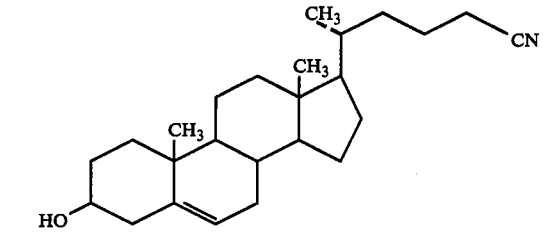

6. In a process for preparing 25-hydroxycholesterol the step of heating a compound having the structure

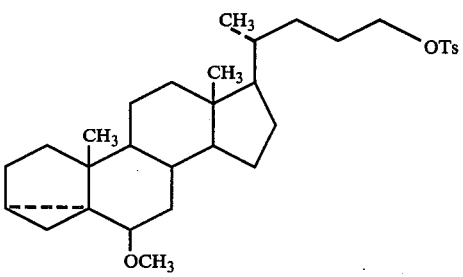

with a metal cyanide in dimethylformamide to obtain a compound having the structure

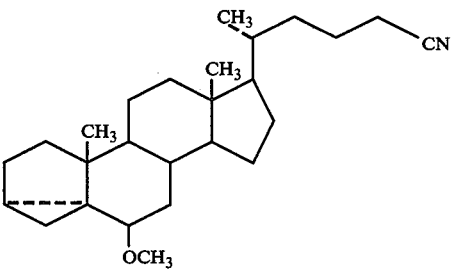

7. A process as set forth in claim 6 including the step of heating the compound having the following structure:

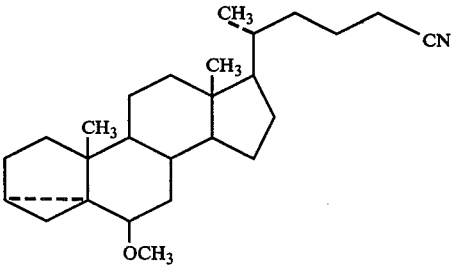

with a water-dioxane mixture containing p-toluenesulfonic acid for a period to complete the reaction and to obtain a compound having the following structure:

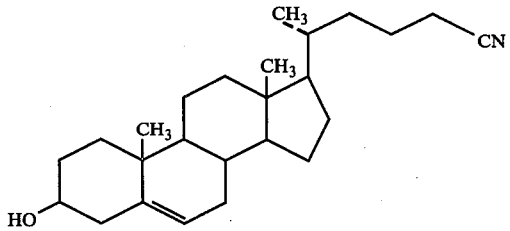

* * * * *